United States Patent [19]

Buck

[11] Patent Number: 4,763,508
[45] Date of Patent: Aug. 16, 1988

[54] METHOD FOR DETERMINING THE FRICTION TORQUE OF A TEST BEARING

[75] Inventor: Volker Buck, Hattingen, Fed. Rep. of Germany

[73] Assignee: Deutsche Forschungs- und Versuchsanstalt fur Luft- und Raumfahrt e.V., Bonn, Fed. Rep. of Germany

[21] Appl. No.: 915,530

[22] Filed: Oct. 6, 1986

[30] Foreign Application Priority Data

Oct. 12, 1985 [DE] Fed. Rep. of Germany ....... 3536474

[51] Int. Cl.[4] ............................................. G01N 19/02
[52] U.S. Cl. ............................................................ 73/9
[58] Field of Search ...................... 73/9, 1 C, 1 B, 763

[56] References Cited

U.S. PATENT DOCUMENTS

| 3,027,749 | 4/1962 | Barnard | 73/9 |
| 3,041,867 | 7/1962 | Knudsen | 73/9 |
| 3,116,628 | 1/1964 | Gordon | 73/9 |
| 3,225,587 | 12/1965 | Gordon | 73/9 |
| 3,685,342 | 8/1972 | Gordon | 73/9 |

FOREIGN PATENT DOCUMENTS

| 0678394 | 8/1979 | U.S.S.R. | 73/9 |
| 0958893 | 9/1982 | U.S.S.R. | 73/9 |

OTHER PUBLICATIONS

U. Milz, "Measurement of Force and Mass Under Influence of Unwanted Acceleration", VDI–Berichte No. 312, 1978, pp. 135–141.

J. Francz, "Die Messung Kleinster Drehmomente bei Kugellagern und Getrieben", Messtechnische Briefe, HBM, 1967, pp. 30–31.

Primary Examiner—Stewart J. Levy
Assistant Examiner—Robert R. Raevis
Attorney, Agent, or Firm—Wolf, Greenfield & Sacks

[57] ABSTRACT

In a method for determining the friction torque of a test bearing, wherein one race member of the test bearing is rotated at a constant rotational speed, while the other race member is connected via a measuring head to a spring acting as force pickup which generates a signal for a measurement of the friction torque of the test bearing, in order to simultaneously enable in a simple manner a high time resolution and calibratability of the friction torque, it is proposed that the motion of the system comprising measuring head and force pickup be damped as little as possible, that in order to calibrate the entire test device, the test bearing be replaced by an air bearing, that with this air bearing arrangement a signal proportional to the spring deformation and a signal proportional to the measuring head acceleration be generated, that a composite signal be formed from the two signals and the relationship of these two signals be set so that they cancel each other out, and that in the measurement of the friction torque of the test bearing, in which case the relationship of the two signals remains unaltered, the composite signal of the two signals be determined as a measure of the friction torque occurring.

2 Claims, 2 Drawing Sheets

METHOD FOR DETERMINING THE FRICTION TORQUE OF A TEST BEARING

BACKGROUND OF THE INVENTION

The invention relates to a method for determining the friction torque of a test bearing, wherein one race member of the test bearing is rotated at a constant rotational speed, while the other race member is connected via a measuring head to a spring acting as a force pickup which generates a signal as a measure of the friction torque of the test bearing.

In the constructions comprising roller bearings, the friction torque is an essential characteristic. Precise knowledge of the friction torque of the bearing utilized in aerospace applications where, for example, in the event of failure of a solar generator drive mechanism, the power available for the satellite is drastically reduced and, consequently, the success of the entire mission is jeopardized, is absolutely essential.

Besides the mean value, in particular, friction torque peaks are of significance. On the one hand, if the driving torque of the motor is exceeded, they can result in failure of the mechanism, on the other hand, such dynamic quantities influence the control behavior of the tracking electronics. Moreover, knowledge of such dynamic quantities and the effects on which they are based, is of interest in elucidating the failure mechanisms of the bearings and, consequently, in fundamental research on the lubrication systems used.

To guarantee the quality of such bearings it is, therefore, necessary to be able to make a calibrated measurement of the friction torque with high time resolution.

A large number of devices for measuring torques and forces is known. Usually, the friction torques are measured reactively via the deformation of an elastic element (spring), with the friction torque being proportional to the deformation of the spring in the static case.

The moment of inertia of the measuring head and the internal damping of the spring material do, however, result in an oscillatory system wherein the friction torque of the measurement bearing and the spring deflection are, as a rule, no longer proportional. For this reason, the strong damping case (aperiodic limiting case) where proportionality between friction torque and spring deformation is attained after a setting time, is usually realized. Such aperiodically damped systems are easy to calibrate using calibrated weights, however, their setting time is too long for many applications.

To reduce the setting time, it is known to measure not only the spring deformation, but also the terms proportional to the acceleration of the test pickup and to the speed of the test pickup (acceleration term and friction term). Using the complete oscillation equation of the test system, the friction torque is then determinable as a function of time. Such a method does indeed result in sufficiently short setting times, but calibration of damping term and acceleration term involves extremely high expenditure and is difficult to survey since no dynamic force standards exist. Such a method has already been described for dynamic disturbance elimination in balances (U. Milz in VDI-Berichte (Association of German Engineers Reports) No. 312, 1978, page 135 et seq.).

The object underlying the invention is to so improve a generic method that the friction torque of a bearing is determinable using extremely simple and precise calibration with high time resolution.

SUMMARY OF THE INVENTION

This object is attained in accordance with the invention in a method of the kind described at the outset by damping the motion of the system comprising measuring head and force pickup as little as possible, by replacing the test bearing by an air bearing, in order to calibrate the entire test device, by generating with this air bearing arrangement a signal proportional to the spring deformation ("A") and a signal proportional to the measuring head acceleration ("B"), by multiplying e.g. signal B with a factor c and forming a composite signal $A + c \cdot B$ from the two signals and setting the factor c so that $A + c \cdot B = 0$ (calibration), and by summing, in the measurement of the friction torque of the test bearing, with unchanged factor c the signals $A'$ corresponding to the spring deformation and $B'$ corresponding to the measuring head acceleration to a composite signal $A' + c \cdot B'$ and taking this composite signal as a measure of the friction torque occurring.

This method enables performance of a first-rate friction torque measurement of high time resolution, such as is required in aerospace applications.

BRIEF DESCRIPTION OF THE DRAWINGS

The following description of preferred embodiments serves in conjunction with the drawings to explain the invention in greater detail. In the drawings.

DETAILED DESCRIPTION OF THE PREFERRED EMBODIMENT

Figure 1:
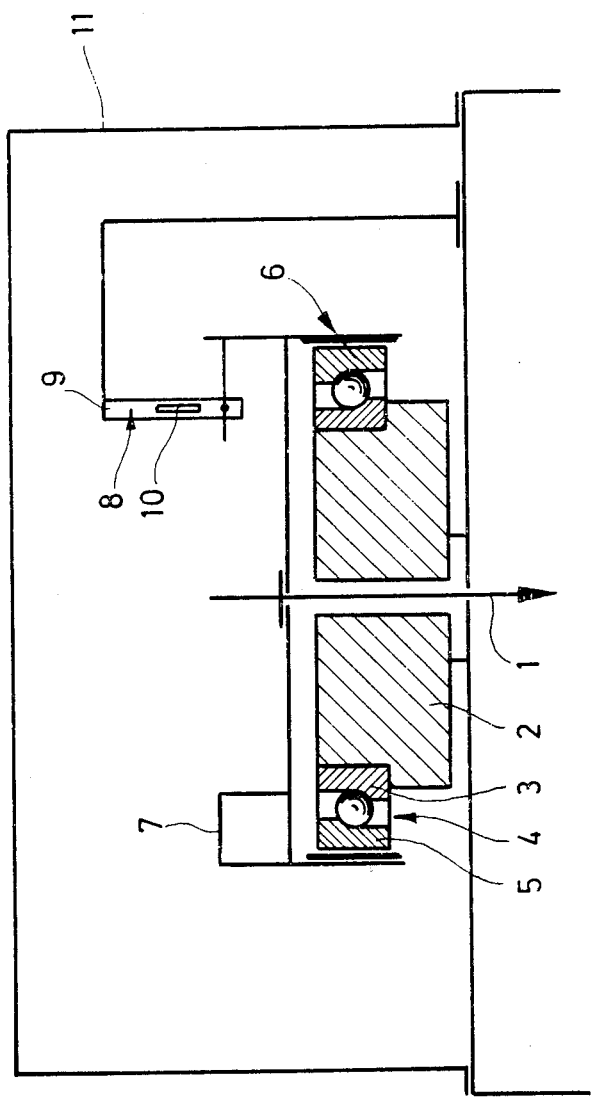
FIG. 1 shows a schematic sectional view of a device for performance of the measurement method.

As shown in FIG. 1, the test device used to determine the friction torque includes a hollow shaft 2 rotatable about a vertical axis of rotation 1, with the inner ring 3 of a ball bearing, referred to hereinafter as test bearing 4, held thereat for rotation therewith. The outer ring 5 of the test bearing 4 is held in a measuring head 6 for rotation therewith. In the illustrated embodiment, the measuring head has the shape of a cylindrical cover. In practice, this cover has substantially larger dimensions than in the illustrated embodiment, for example, a substantially thicker bottom since additional devices, for example, hydraulic tensioning elements to simulate different temperature expansions of the various parts of the test bearing, are arranged in this measuring head.

The measuring head 6 is mounted by means of the test bearing 4 for rotation on the hollow shaft 2. The hollow shaft 2 can be continuously rotated, for example, at a rotational speed of 1 to 2 revolutions per minute, by a drive which is not illustrated in the drawing.

An accelerometer 7 which supplies an electrical signal proportional to the rotary acceleration is arranged on the measuring head 6.

The measuring head 6 is, furthermore, supported at a spring 8 whose one end 9 is stationarily mounted. The arrangement of the spring 8 is such that it undergoes deformation, upon rotation of the measuring head 6 from a position of rest, and attempts to elastically turn the measuring head 6 back into the rest position. Strain gauges 10 which supply an electrical signal corresponding to the deformation of the spring 8 are connected to the spring.

The entire arrangement is disposed in receptacle 11.

Figure 2:
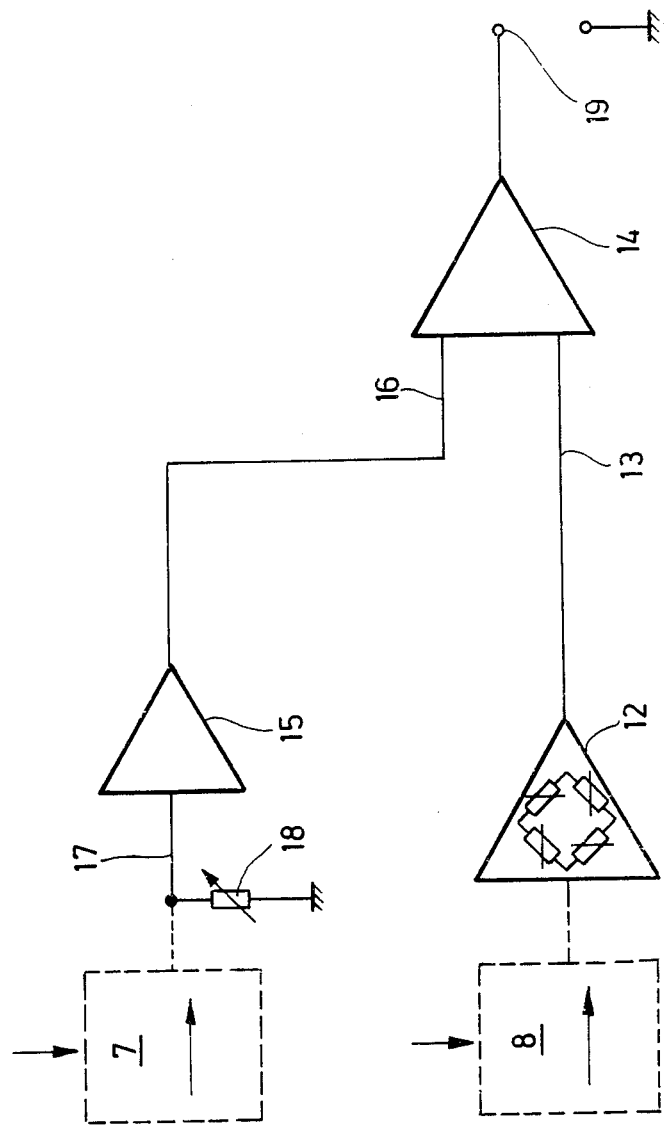
FIG. 2 shows a schematic connection diagram of a circuit for generating a composite signal as a measure of the friction torque transmitted by the test bearing.

The electrical signals generated by the accelerometer 7 and by the strain gauges 10 are fed to the electric circuit illustrated in FIG. 2. The deflection of the spring is converted via the strain gauges in a full bridge circuit 12 into an electrical signal which is fed to the one input 13 of a summing amplifier 14.

A signal of the accelerometer 7 which, on account of the disappearing low limiting frequency, is preferably in the form of a servo acceleration pickup, is fed via an amplifier 15 to the other input 16 of the summing amplifier 14. The current produced by the accelerometer 7 is fed via a variable resistor 18 to ground, so that the voltage occurring at the output of amplifier 15 can be altered.

The entire arrangement illustrated in FIG. 1 constitutes an oscillatory system which obeys the following equation:

$$\theta\ddot{\phi}(t) + \beta\dot{\phi}(t) + D^*\phi(t) = M_{bearing}(t) \qquad (I)$$

where:
$\theta$: moment of inertia of the measurement head
$\beta$: friction coefficient
$D^*$: spring constant
$\phi(t)$: angular position of the measuring head as a function of time
$\dot{\phi}(t)$: angular speed of the measuring head as a function of time
$\ddot{\phi}(t)$: angular acceleration of the measuring head as a function of time
$M_{bearing}(t)$: friction torque of the test bearing as a function of time The friction of damping of the measuring head proportional to the angular speed is practically exclusively due to the internal damping of the spring 8 and is extremely low. It is therefore possible to neglect the friction term $\beta\dot{\phi}(t)$ in relation to the other terms.

The spring term can be readily calibrated in a static test, for example, by deforming the spring with a defined force using calibrated weights.

In the method described herein, the test bearing is first replaced by an air bearing, so as to be able to take the influences of the inertia term $\theta\ddot{\phi}(t)$ into account. This bearing arrangement has an outer portion associated with the measuring head and an inner portion associated with the hollow shaft, which are held in mutually spaced relationship by an outflow of air such that the measuring head is rotatable relative to the hollow shaft in a practically frictionless manner.

In such an arrangement, the bearing friction $M_{bearing}(t)$ becomes neglectably small, so that the following oscillation equation applies to this arrangement:

$$\theta\ddot{\phi}(t) + D^*\phi(t) = 0 \qquad (II)$$

The electrical signal generated by the accelerometer 7 is proportional to the inertia term $\theta\ddot{\phi}(t)$, the electrical signal of the strain gauges on the spring 8 to the deformation term $D^*\phi(t)$. If these two electrical signals are set in their mutual relationship such that the composite signal of the two signals equals zero, the behavior of the electrical signals then occurring corresponds precisely to the oscillation equation II of the system. This is attainable in a simple manner by striking the measuring head in the air bearing arrangement which then executes a free oscillation. During this free oscillation, the value of the variable resistor 18 is altered such that the signal disappears at the output 19 of the summing amplifier 14. Accordingly, a simple zero-balancing method is obtained, with which the acceleration term can be calibrated in relation to the spring term.

To measure the friction torque of a test bearing, it is now inserted into the arrangement in lieu of the air bearing. The setting of the variable resistor 18 remains unaltered, so that also the relationship of the electrical signals of the accelerometer and the strain gauges of the spring remains identical. This then ensures that at each point in time the composite signal at the output 19 of the summing amplifier 14 is proportional to the friction torque of the test bearing. Since it is possible to statically calibrate the spring term in the above-described manner, and as the inertia term can also be calibrated in a simple manner by the zero-balancing method, it is thus also possible to determine the absolute quantity of the friction torque of the test bearing on the basis of the composite signal at the output 19 of the summing amplifier 14.

In the course of such a measurement, the measuring head executes torsional vibrations, and the amplitude of these torsional vibrations will, as a rule, be substantially greater than the rotation corresponding to the friction torque of the bearing. The influence of these oscillations is, however, compensated by the described processing of the signals of the accelerometer, on the one hand, and of the strain gauges of the spring, on the other hand, to such an extent that the remaining composite signal at the output 19 of the summing amplifier 14 is unaffected by these oscillations of large amplitude and changes only proportionally to the behavior of the friction torque of the test bearing as a function of time.

With the arrangement illustrated in FIG. 1, it is possible to attain, in accordance with the limiting frequency of the accelerometer used, for example, a limiting frequency of the test arrangement of approximately 300 hertz.

What is claimed is:

1. A method for determining the friction torque of a test bearing wherein a first race member of the test bearing is rotated at a constant rotational speed, while a second race member bearing a measuring head is connected to a force pickup spring, wherein the motion of the system comprising said force pickup spring and said second race member bearing said measuring head is damped as little as possible, wherein the improvement comprises:

A. calibrating signal generation of said measuring head and said force pickup by
  (i) replacing said test bearing with an air bearing and striking said second race member bearing said measuring head to initiate a free oscillation of said measuring head,
  (ii) generating a first signal A proportional to the deformation of said pickup spring,
  (iii) generating a second signal B proportional to the acceleration of said measuring head during said free oscillation,
  (iv) forming a first composite signal $A + c \times B$ of said first and second signals, A and B respectively, by adding the first signal A and the second signal B multiplied by a factor c, and
  (v) adjusting said factor c to a setting such that said first composite signal becomes zero; and
 B. measurement signal generation by (i) replacing said air bearing with said test bearing and rotating said first race member at a constant rotational speed, (ii) generating a third signal A' proportional to the deformation of said pickup spring, (iii) generating a fourth signal B' proportional to the acceleration of said measuring head during said constant rotation of the first race member, (iv) forming a second composite signal $A' + c \times B'$ with the setting of said factor c remaining unaltered, whereby said second composite signal provides said measurement signal to measure the friction torque of said test bearing.

2. The improved friction torque determination method of claim 1 wherein said force pickup comprises a spring and said first signal is proportional to the deformation of said spring during said rotation.

* * * * *